United States Patent [19]
Pesque et al.

[11] Patent Number: 5,718,229
[45] Date of Patent: Feb. 17, 1998

[54] MEDICAL ULTRASONIC POWER MOTION IMAGING

[75] Inventors: Patrick René Pesque, Bothell; Roy Beck Peterson, Redmond; Jens Ulrich Quistgaard, Seattle, all of Wash.

[73] Assignee: Advanced Technology Laboratories, Inc., Bothell, Wash.

[21] Appl. No.: 655,394

[22] Filed: May 30, 1996

[51] Int. Cl.⁶ .................................................. A61B 8/00
[52] U.S. Cl. ...................................................... 128/660.05
[58] Field of Search ......................... 128/660.04, 660.05, 128/660.07, 661.04, 661.08, 661.09, 661.1, 661.07; 73/861.25

[56] References Cited

U.S. PATENT DOCUMENTS

| | | | |
|---|---|---|---|
| 4,799,490 | 1/1989 | Namekawa | 128/661.09 |
| 4,928,698 | 5/1990 | Bonnefous | 128/661.09 |
| 5,197,477 | 3/1993 | Peterson et al. | 128/661.08 |
| 5,224,481 | 7/1993 | Ishihara et al. | 128/660.07 |
| 5,233,993 | 8/1993 | Kawano | 128/660.07 |
| 5,241,473 | 8/1993 | Ishihara et al. | 364/413.25 |
| 5,285,788 | 2/1994 | Arenson et al. | 128/660.05 |
| 5,419,328 | 5/1995 | Goh et al. | 128/660.07 |
| 5,544,659 | 8/1996 | Banjanin | 128/661.09 |

*Primary Examiner*—George Manuel
*Attorney, Agent, or Firm*—W. Brinton Yorks, Jr.

[57] ABSTRACT

An ultrasonic imaging system is provided which produces signals representative of tissue motion through amplitude detection of echo signals from which stationary clutter has been removed. Tissue motion may be distinguished from noise and flow signals on the basis of the dynamic range of the detected signals. The tissue motion signals may be displayed in combination with B mode signals to augment images of moving tissue, or in a two dimensional image in combination with B mode and Doppler image information. A sequence of gated tissue motion images of the heart may be displayed with each image of a different phase of the heart cycle displayed in a different color. The sequence may be played in a real time sequence, or the images accumulated in a common static image which overlay and hence mask one another, thereby revealing subtle differences in motion from one phase of the heart cycle to another.

21 Claims, 4 Drawing Sheets

MEDICAL ULTRASONIC POWER MOTION IMAGING

This invention relates to medical ultrasonic diagnostic imaging techniques and, in particular, to the ultrasonic diagnostic imaging of moving tissue within the body.

Medical ultrasonic imaging systems have been quite adept at imaging tissue and blood flow for a number of years. Tissue is imaged by B mode imaging techniques and blood flow is conventionally imaged with Doppler techniques, which attempt to measure or estimate a Doppler phase or frequency shift of a received echo from moving blood cells. However, there is physiology within the body which possesses characteristics of both tissue and blood flow, which is moving tissue. Moving tissue, such as the walls of the beating heart, will reflect ultrasonic echoes in the same manner as any other tissue within the body. But moving tissue will also return ultrasonic echoes which can be processed to determine the Doppler shift of the echo information by virtue of its motion. Hence, attempts have been made to image moving tissue through Doppler processing of echoes returned from moving tissue as described in U.S. Pat. No. 5,285,788.

Doppler tissue imaging has a number of deficiencies, however. For one, Doppler frequency analysis requires a significant amount of temporal echo information. The time required to acquire this temporal information delays the production of Doppler information for display, slowing the frame rate of display. Another limitation is the lack of sufficient motion sensitivity. When narrowband systems such as that shown in the '788 patent are employed for Doppler processing, the limited phase characteristics of the narrowband signals reduce the sensitivity of the moving tissue display. By contrast, broad bandwidth signals allow better axial resolution and, together with a tightly focused beam, enable the detection of smaller movements. Furthermore, Doppler systems such as that of the '788 patent are insensitive to motion normal to the ultrasound beam, resulting in undesirable angle sensitivity and signal dropout. Accordingly there is a need for techniques for imaging moving tissue which overcome the deficiencies of the '788 patent and other techniques.

In accordance with the principles of the present invention an ultrasonic technique for imaging moving tissue is presented which overcomes these deficiencies of the prior art. A region to be imaged is insonified with ultrasonic energy. Two spatially aligned, temporally different echoes from each sample volume being imaged are applied to a stationary canceller or moving target indicator to remove stationary clutter. The preferred stationary canceller is a pulse to pulse subtractor which subtracts consecutive received echoes from a particular spatial location. With echoes from stationary targets removed, the received signals are amplitude detected. The detected signals undergo discrimination to distinguish moving tissue from blood flow and noise, and the resultant moving tissue signals are displayed. The moving tissue information may be displayed simultaneously with B mode information of neighboring stationary tissue, and/or with Doppler information of fluid flow. A cross sectional view of the beating heart can be displayed with color Doppler flow information added to fill in the heart chambers of the image. A preferred display technique is a realtime display of images of the heart acquired at different phases of its cycle of operation, each in a different color. As the heart beats, abnormalities can be distinguished by the color in which they appear, and the image of the noted color can be displayed as a stationary image for diagnosis. A color bar display is described for distinguishing heart cycle phases and adjusting the displayed phases of the heart.

Figure 1:
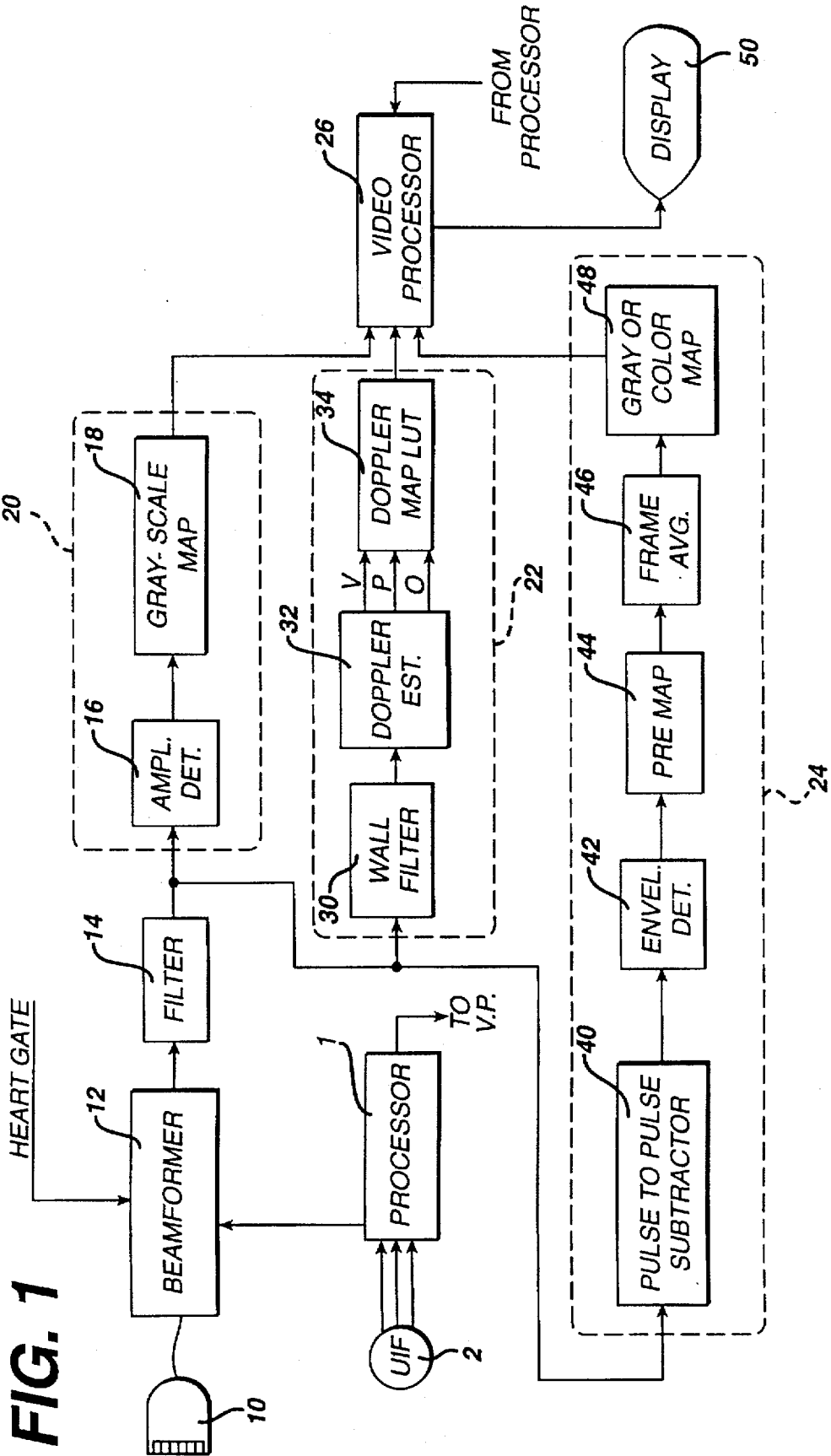
FIG. 1 is a block diagram of an ultrasonic diagnostic imaging system constructed in accordance with the principles of the present invention.
Figure 2:
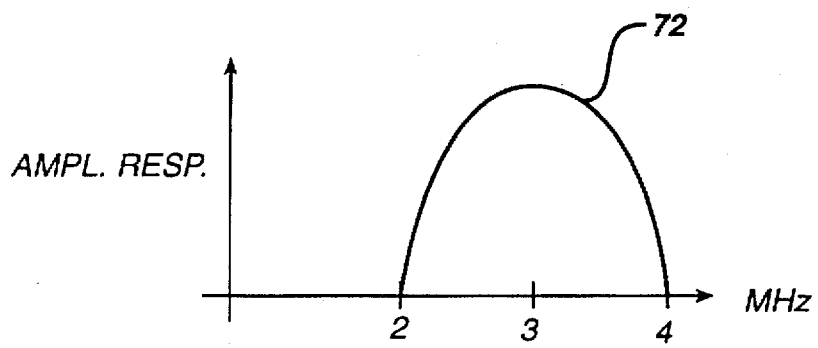
FIG. 2 illustrates a filter response characteristic described in the discussion of FIG. 1.

Referring to FIG. 1, a block diagram of an ultrasonic diagnostic imaging system constructed in accordance with the principles of the present invention is shown. A scanhead 10 transmits ultrasonic pulses and receives ultrasonic echoes. Preferably, as described below, the scanhead is a broadband scanhead for reasons discussed below. The scanhead 10 is controlled by a beamformer 12, which controls the timing of transmission by the scanhead and forms coherent echo signals from the individual echoes received by the elements of the scanhead. The coherent echo signals are then filtered by a bandpass filter 14, which removes noise outside the passband of the scanhead. For a 3 MHz center frequency scanhead, the filter 14 may exhibit a 2 MHz passband as illustrated in FIG. 2. The filtered echo signals are then processed for display by a B mode processor 20, a Doppler processor 22, or a power motion image processor 24. Image information from each processor is coupled to a video processor 26 and displayed on a display monitor 50.

In FIG. 1 the B mode processor 20 includes an amplitude detector 16 which detects the amplitude of the echo signals. A preferred form of amplitude detection operates upon the I and Q quadrature signal components produced by the beamformer 12 and computes amplitude by the expression $(I^2+Q^2)^{1/2}$. The detected B mode signals then undergo log compression and scaling in a grayscale mapping circuit 18, which produces grayscale signals in correspondence with the detected amplitudes of the B mode signals. The grayscale signals, which can be presented as various shades of a black and white display or various brightness levels of a color display, are processed by the video processor 26 and displayed on display 50.

The Doppler processor 22 includes a wall filter 30 to remove echoes returned from heart and vessel walls. A preferred wall filter which also removes artifacts termed flash which are due to scanhead motion is described in U.S. Pat. No. 5,197,477. A Doppler estimator 32 processes ensembles of scanline information to estimate the Doppler shift evidenced by the received echo signals. As is known in the art, the Doppler shift or frequency can be estimated by autocorrelation, Fourier transform processing, and the like. The Doppler shift signals can be used to present velocity, Doppler power, variance, and other Doppler information. The Doppler information is mapped by a Doppler color mapping circuit 34 conventionally in the form of a look up table and transmitted to the video processor 26 for display. As is known in the art, color Doppler information may be simultaneously displayed with B mode information to depict blood or other fluid flow in the heart, blood vessels, and other organs of the body.

Figure 3:
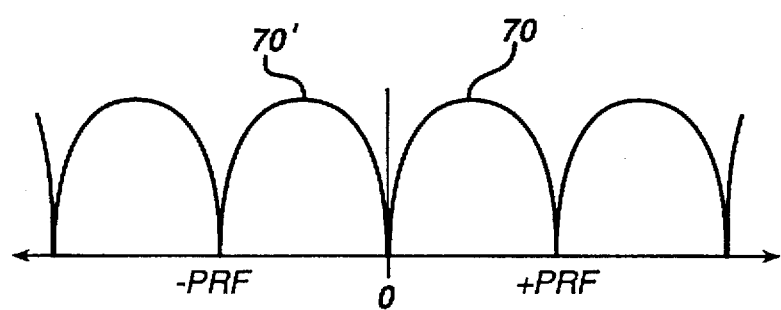
FIG. 3 illustrates the response characteristic of the pulse to pulse subtractor of FIG. 1.

The power motion image processor 24 of the present invention includes a pulse to pulse subtractor 40 which computes the difference in temporally separate echo signals received from the same resolution cell. The pulse to pulse subtractor 40 will thereby remove echoes returned from stationary objects at the resolution cell location. The temporal difference can derive from echoes returned following two pulse transmissions to the location within the time that a frame of echo information is acquired, or can derive from pulse transmissions to the location during the acquisition of different frames of information. While other stationary clutter rejection filters can be employed such as wall filters and moving target indicators, the pulse to pulse subtractor is preferred by reason of the short duration required to transmit and receive two echoes. Furthermore, the response of the subtractor is variable by adjustment of coefficients employed in the computation. The pulse to pulse subtractor 40 performs a computation of the form $aP_A - bP_B$ where a and b are weighting coefficients of the echoes received from a given location in response to temporally distinct pulses A and B. The response characteristic for the subtractor is as shown in FIG. 3 for the condition where a and b each have a value of one, where PRF is the repetition interval between the two pulses. Variation of the coefficient values varies the depth of the rejection notches of the characteristic at the PRF intervals. For example, if a is 1.1 and b is 0.9, the DC response at the rejection notches is 0.2, or 20 dB down from the response peaks. When the coefficients are each 1.0, the DC response is zero, an infinite rejection level. Thus, the sensitivity of the subtractor to motion can be varied by varying the coefficients.

Multiple computations using different coefficients can alter the sensitivity of the subtractor and overcome pulsatile effects such as the low level of motion at end diastole. For instance, a digital filter can be used to perform a three echo subtraction of the form $aP_A + bP_{B+CPC}$, where a=+1, b=−2 and c=+1. A two pulse subtraction is preferred, however, for its high frame rate real time display.

Figure 4:
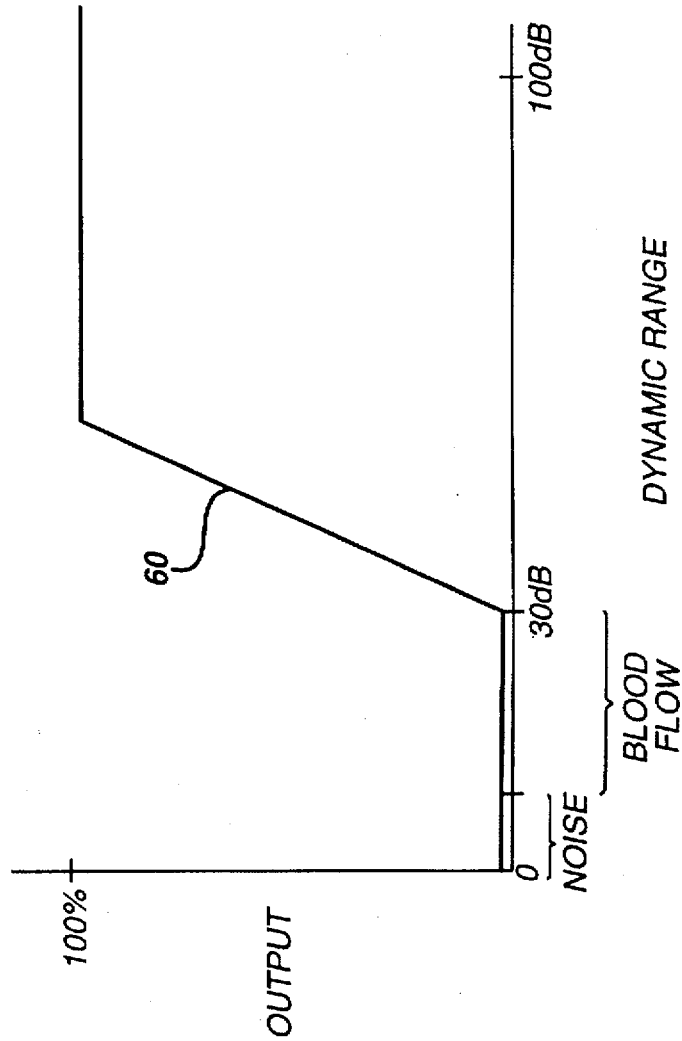
FIG. 4 illustrates the characteristic of the premap of FIG. 1.

The echo values remaining subsequent to stationary clutter rejection then undergo envelope or amplitude detection in a circuit 42. The detected signals undergo discrimination for tissue motion in a premap circuit 44. A preferred premap circuit exhibits a characteristic such as that shown in FIG. 4, whereby an output signal is produced as a function of the dynamic range of the applied echo signal. In the example of FIG. 4, low amplitude signals are considered to be noise, and signals above the noise level and below 30 dB are considered to result from blood flow. Signals from 30 dB to above 100 dB are considered to result from moving tissue, and produce an output signal as indicated by response curve 60. The detected motion signals may then be temporally averaged on a frame basis by frame averaging circuit 46. The temporally averaged signals are then mapped by a gray or color mapping circuit 48. The moving tissue signals may be displayed in black and white by gray mapping the signals, or in color by a color map. One consideration as to the type of mapping to employ is the other types of signals with which the moving tissue signals are to be displayed. For instance, moving tissue signals of the beating heart produced by the power motion imaging circuit 24 can be produced as black and white signals and blended with B mode heart signals to augment the B mode display. The chambers of the heart can be filled with color flow display information produced by the Doppler processor 22. The resultant display is thus a combination of B mode, Doppler, and power motion signals. Another combination is to use the power motion signals to display the beating heart in one color and power Doppler or color flow Doppler signals from the Doppler processor 22 to show the blood flow in the heart chambers in another color or range of colors.

Figure 5:
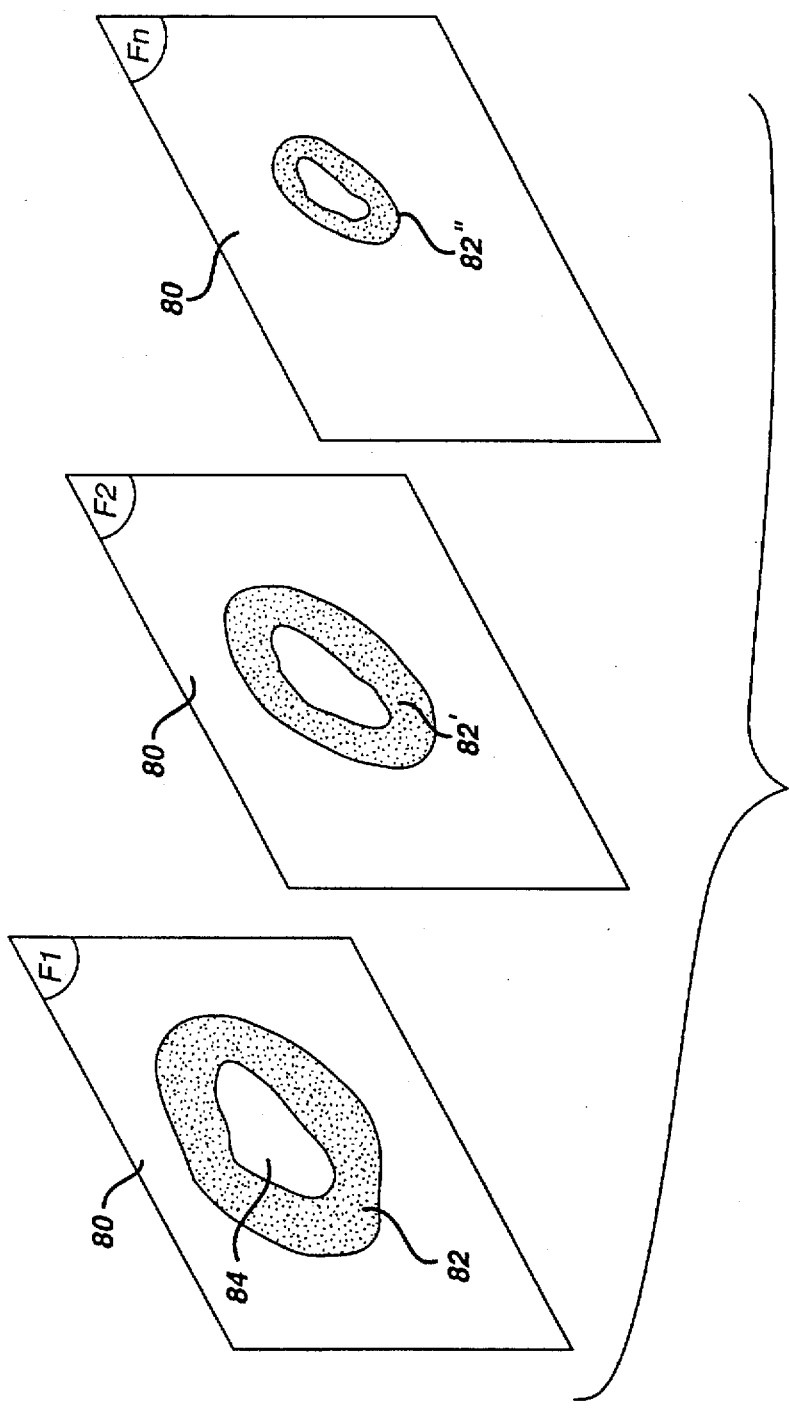
FIG. 5 illustrates a sequence of ultrasonic images of the heart acquired at different phases of the heart cycle.
Figure 6:
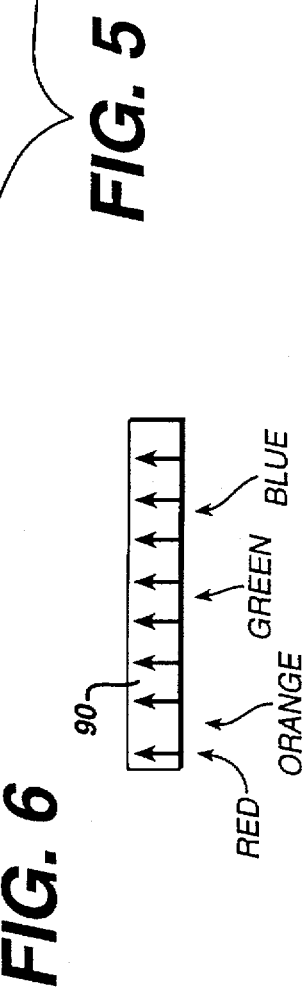
FIG. 6 illustrates a color bar identifying the colors of images of different phases of the heart cycle.

A preferred power motion display technique is shown in FIGS. 5 and 6. FIG. 5 shows a sequence of ultrasonic image frames 80, respectively identified as F1, F2, ... Fn, each of which was acquired at a specific phase of the heart cycle. Such image frames can be acquired by gated acquisition of image information using an ECG heart gate as shown in FIG. 1. In the exemplary frames of FIG. 5, frame F1 shows the myocardium fully relaxed at end diastole. The subsequent image frames depict the myocardium during successively contracted phases as it approaches systole. The myocardium 82' is contracted somewhat in frame F2, and the myocardium 82" is shown fully contracted in the last frame Fn.

Each image frame in the F1 ... Fn sequence is displayed in a different color. FIG. 6 illustrates a color bar 90 which displays a spectrum of colors from one end to the other. In the example of FIG. 6 the color bar spectrum starts with red and varies through orange, then green, then blue. The arrows located along the color bar mark the relative separation of the times of acquisition of the image frames in FIG. 5. The myocardium 82 in the first frame F1 would be colored red, the myocardium 82' in frame F2 is orange, and the myocardium 82" of the last frame Fn would be dark blue or violet, for example. The operator of the imaging system can set the number and relative positions of the arrows for the acquisition times by manipulating controls on the user interface 2 in FIG. 1. The settings dictated by the user interface controls are received and processed by a system processor 1 to develop control signals for the beamformer 12 controlling the heart phases of signal acquisition and for the video processor to control the colors in which the myocardium is to be displayed in each image frame.

After the F1 ... Fn image frame sequence has been acquired it is displayed in real time. It may be repetitively displayed by storing the sequence and replaying it from Cineloop® memory, for instance. As the sequence is replayed, the eye can correlate any defect or abnormality in movement of the myocardium with the color in which the myocardium is displayed at that instant. The user can stop the real time display and display the single colored image in which the defect or abnormality appeared for more detailed study and diagnosis.

A high resolution imaging system practicing the present invention with small resolution cells is more sensitive to motion than systems with lower resolution. High resolution is achieved in the axial dimension by using broadband signals as opposed to narrowband signals. High resolution is achieved in the lateral dimension by a tightly focused beam. Elevation focus can narrow the beam in the elevation dimension. The high sensitivity to motion exhibited by an embodiment of the present invention is in sharp contrast to Doppler techniques, where the inherent angle dependency causes a loss of lateral sensitivity to motion.

In the claims:

1. An ultrasonic imaging system which processes received echo signals for the display of moving tissue comprising:

a receiver which produces echo signals;

a moving target indicator responsive to temporally different echoes from a common spatial location which eliminates stationary clutter;

an amplitude detector, coupled to said moving target indicator, for detecting signals from which stationary clutter has been eliminated; and a display for displaying said detected signals.

2. The ultrasonic imaging system of claim 1, further comprising:

a discriminator responsive to said detected signals for distinguishing signals resulting from moving tissue.

3. The ultrasonic imaging system of claim 2, wherein said discriminator comprises means for identifying moving tissue signals as a function of the dynamic range of applied signals.

4. The ultrasonic imaging system of claim 1, wherein said moving target indicator comprises a pulse to pulse subtractor.

5. The ultrasonic imaging system of claim 4, wherein said pulse to pulse subtractor includes means for weighting the temporally different echo values from which differences are computed by said pulse to pulse subtractor.

6. The ultrasonic imaging system of claim 1, wherein said moving target indicator comprises a stationary canceller.

7. The ultrasonic imaging system of claim 1, wherein said amplitude detector comprises an envelope detector.

8. The ultrasonic imaging system of claim 1, wherein said amplitude detector processes signals from which stationary clutter has been removed in accordance with the expression $(I^2+Q^2)^{1/2}$.

9. The ultrasonic imaging system of claim 1, further comprising a B mode image processor.

10. The ultrasonic imaging system of claim 9, further comprising a video processor for producing a display of blended B mode image and moving tissue signals.

11. The ultrasonic imaging system of claim 1, further comprising a Doppler image processor.

12. The ultrasonic imaging system of claim 11, further comprising a video processor for producing an image of moving tissue and Doppler fluid flow.

13. The ultrasonic imaging system of claim 1, further comprising a B mode image processor and a Doppler image processor.

14. An ultrasonic imaging system which processes received echo signals for the display of moving tissue comprising:

a receiver which produces echo signals;

a moving tissue processor, responsive to said echo signals for producing signals representative of moving tissue;

means for producing moving tissue images at specific phases of the heart cycle; and means, responsive to said means for producing moving tissue images at specific phases of the heart cycle, for displaying said moving tissue images of different heart phases in different colors.

15. The ultrasonic imaging system of claim 14, further comprising means for displaying said different color moving tissue images in a real time sequence.

16. The ultrasonic imaging system of claim 15, further comprising a color display depicting the colors of said moving tissue images among a range of colors.

17. The ultrasonic imaging system of claim 16, wherein said color display comprises a color bar in correspondence with which the times of acquisition of said moving tissue images are shown.

18. An ultrasonic imaging system which processes received echo signals for the display of moving tissue comprising:

a receiver which produces echo signals;

a circuit responsive to said echo signals for eliminating stationary clutter signals;

an amplitude detector, coupled to receive signals processed by said stationary clutter eliminating circuit; and a display for displaying said detected signals.

19. An ultrasonic imaging system comprising:

a receiver for receiving echo signals;

a B mode processor coupled to process received echo signals for the production of B mode image signals;

a Doppler processor coupled to process received echo signals for the production of image signals containing Doppler information; and a tissue motion processor coupled to process received echo signals for the production of amplitude detected tissue motion image signals; and a video processor, coupled to said B mode processor, said Doppler processor, and said tissue motion processor for producing images which include image signals processed by two of said echo signal processors.

20. The ultrasonic imaging system of claim 19, wherein said video processor produces images in which B mode processed signals and tissue motion signals are blended together.

21. The ultrasonic imaging system of claim 19, wherein said video processor produces images containing B mode processed signals, Doppler processed signals, and tissue motion signals.

* * * * *